United States Patent
Negele et al.

Patent Number: 5,420,293
Date of Patent: May 30, 1995

[54] N-SUBSTITUTED α-FLUOROALKYL-LACTAMS

[75] Inventors: Michael Negele, Solingen; Norbert Lui, Cologne; Bernd Baasner, Bergisch Gladbach; Gerd Hänssler, Leverkusen, all of Germany

[73] Assignee: Bayer Aktiengesellschaft, Leverkusen, Germany

[21] Appl. No.: 179,803

[22] Filed: Jan. 11, 1994

[30] Foreign Application Priority Data

Jan. 18, 1993 [DE] Germany ............... 43 01 112.8

[51] Int. Cl.⁶ ................................. C07D 207/26
[52] U.S. Cl. ......................... 548/550; 424/404; 424/405; 548/537
[58] Field of Search ........... 548/550, 537; 424/404, 424/405; 514/424

[56] References Cited

U.S. PATENT DOCUMENTS

| | | | |
|---|---|---|---|
| 3,404,147 | 10/1968 | Mayhew et al. | 260/239.3 |
| 5,171,355 | 12/1992 | Negele et al. | 71/95 |
| 5,254,696 | 10/1993 | Negele et al. | 548/531 |
| 5,256,795 | 10/1993 | Negele et al. | 548/531 |

FOREIGN PATENT DOCUMENTS 0201742  11/1986  European Pat. Off. .

*Primary Examiner*—David B. Springer
*Attorney, Agent, or Firm*—Sprung Horn Kramer & Woods

[57] ABSTRACT

The new N-substituted α-fluoroalkyl-lactams of the general formula

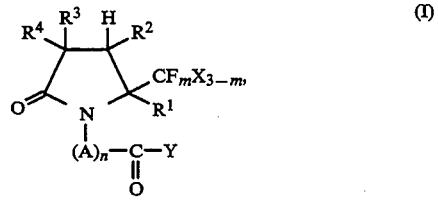

in which the substituents and indices have the meaning indicated in the description, exhibit a strong action against pests and can be employed in particular for combating unwanted fungi.

7 Claims, No Drawings

N-SUBSTITUTED α-FLUOROALKYL-LACTAMS

The present invention relates to a new N-substituted α-fluoroalkyl-lactams, to new intermediates, to a process for the preparation of the new N-substituted α-fluoroalkyl-lactams, and to their use as pest control agents.

The new N-substituted α-fluoroalkyl-lactams correspond to the general formula

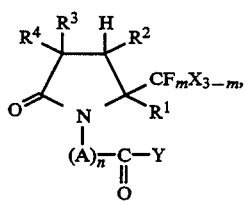

in which
  $R^1$ represents hydrogen, halogen, cyano, alkyl, aryl or alkoxycarbonyl,
  $R^2$ and $R^3$ independently of one another represent hydrogen, halogen, alkyl or aryl,
  $R^4$ represents hydrogen, halogen, cyano, alkyl, aryl or alkoxycarbonyl,
  A represents alkylene,
  Y represents alkoxy, amino, (di)alkylamino or aryl, or Y together with the radical $R^1$ represents alkylene,
  n represents 0 or 1,
  X represents hydrogen, halogen or alkyl, and
  m represents 1, 2 or 3.

All alkyl radicals can be straight-chain or branched. Furthermore, all alkyl, alkoxy, aryl and alkylene radicals even when they occur in composite terms such as, for example, alkoxycarbonyl, can optionally be substituted.

The new N-substituted α-fluoroalkyl-lactams of the formula (Ia)

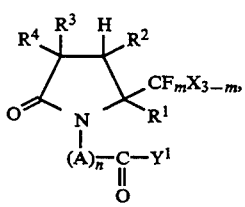

in which
  $R^1$, $R^2$, $R^3$, $R^4$, A, X, m and n have the meaning given for formula (I), and
  $Y^1$ represents alkoxy or aryl,
can be prepared by reacting pyrrolidinone derivatives of the formula

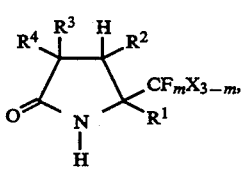

in which
  $R^1$, $R^2$, $R^3$, $R^4$, X and m have the meaning given above with compounds of the formula

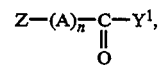

in which
  Z represents halogen, in particular bromine or chlorine, and
  A, $Y^1$ and n have the meaning given above,
optionally in the presence of a diluent and optionally in the presence of an acid-binding agent.

The new N-substituted α-fluoroalkyl-lactams of the formula (Ib)

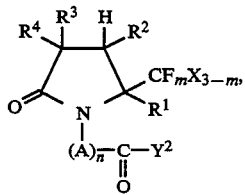

in which
  $R^2$, $R^3$, $R^4$, A, X, m and n have the meaning given for formula (I), and
  $Y^2$ together with the radical $R^1$ represents alkylene
can be prepared by reacting compounds of the formula

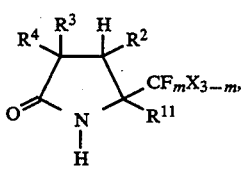

in which
  $R^{11}$ represents optionally substituted alkoxycarbonylalkyl, preferably optionally substituted $C_1$-$C_4$-alkoxycarbonyl-$C_1$-$C_4$-alkyl, and
  $R^2$, $R^3$, $R^4$, X and m have the meaning given above, with a base, preferably with an alkali metal hydroxide, and subsequently reacting the resulting product with a water-binding agent such as, for example, an acid anhydride, preferably acetic anhydride, in each case optionally in the presence of a diluent.

The new N-substituted α-fluoroalkyl-lactams of the formula (Ic)

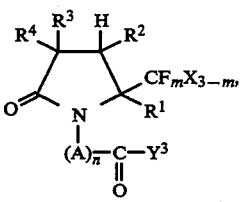

in which
  $R^1$, $R^2$, $R^3$, $R^4$, A, X, n and m have the meaning given for formula (I), and
  $Y^3$ represents amino or (di) alkylamino, preferably amino, $C_1$-$C_4$-alkylamino or $C_1$-$C_4$-dialkylamino each of which is optionally substituted by (di)-$C_1$-$C_4$-alkylamino,
can be prepared by reacting compounds of the formula (Id)

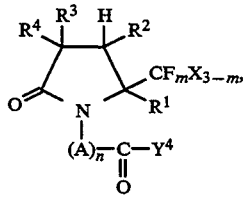

in which
R$^1$, R$^2$, R$^3$, R$^4$, A, X, n and m have the meaning given for the formula (I), and
Y$^4$ represents alkoxy, preferably C$_1$–C$_4$-alkoxy,
with an amine of the formula (V)

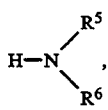

in which
R$^5$ and R$^6$ independently of one another represent hydrogen or C$_1$–C$_4$-alkyl which is optionally substituted by (di)-C$_1$–C$_4$-alkylamino.

Finally, it has been found that the new N-substituted α-fluoroalkyl-lactams possess a good activity as fungicides.

A general definition of the new N-substituted α-fluoroalkyl-lactams according to the invention is given by the formula (I). Preferred compounds of the formula (I) are those in which
R$^1$ represents hydrogen, fluorine, chlorine, bromine, optionally substituted C$_1$–C$_6$-alkyl, optionally substituted C$_6$–C$_{10}$-aryl or optionally substituted C$_1$–C$_6$-alkoxycarbonyl(C$_1$–C$_4$)-alkyl,
R$^2$ and R$^3$ independently of one another represent hydrogen, fluorine, chlorine, bromine, optionally substituted C$_1$–C$_6$-alkyl or optionally substituted C$_6$–C$_{10}$-aryl,
R$^4$ represents hydrogen, fluorine, chlorine, bromine, cyano, optionally substituted C$_1$–C$_6$-alkyl, optionally substituted C$_6$–C$_{10}$-aryl or optionally substituted C$_1$–C$_6$-alkoxycarbonyl,
A represents optionally substituted C$_1$–C$_4$-alkylene,
Y represents optionally substituted C$_1$–C$_6$-alkoxy, amino, optionally substituted C$_1$–C$_6$-alkylamino, optionally substituted C$_6$–C$_{10}$-dialkylamino or optionally substituted C$_6$–C$_{10}$-aryl, or
Y together with the radical R$^1$ represents optionally substituted C$_1$–C$_4$-alkylene,
n represents 0 or 1,
X represents hydrogen, fluorine, chlorine, bromine or optionally substituted C$_1$–C$_4$-alkyl, and
m represents 1, 2 or 3,
possible substituents for the alkyl and alkoxy radicals mentioned in the definitions of R$^1$, R$^2$, R$^3$, R$^4$, X and Y, and for the alkylene radicals in the definitions of A and Y, and for the radical alkoxycarbonylalkyl in the definition of R$^1$ being in each case fluorine, chlorine, bromine, hydroxyl, methoxy and ethoxy, possible (di)alkylamino radicals in the definition of Y being (di)methylamino, (di)ethylamino or (di)isopropylamino, and possible substituents for aryl in the definitions of R$^1$, R$^2$, R$^3$, R$^4$ and Y being in each case fluorine, chlorine, bromine, C$_1$–C$_4$-alkyl and C$_1$–C$_4$-alkoxy.

Compounds of the formula (I) are particularly preferred in which
R$^1$ represents hydrogen, fluorine, chlorine, bromine, methyl, ethyl, n-propyl, i-propyl, n-butyl, s-butyl, i-butyl, t-butyl, phenyl, naphthyl, methoxycarbonylmethyl, methoxycarbonylethyl, ethoxycarbonylmethyl or ethoxycarbonylethyl,
R$^2$ represents hydrogen, fluorine, chlorine, bromine, methyl, ethyl, phenyl or naphthyl,
R$^3$ represents hydrogen, fluorine, chlorine, bromine, methyl or ethyl,
R$^4$ represents hydrogen, fluorine, chlorine, bromine, cyano, methyl, ethyl, phenyl, methoxycarbonyl or ethoxycarbonyl,
A represents —CH$_2$— or —CH$_2$CH$_2$—,
Y represents methoxy, ethoxy, amino, or represents (di)methylamino or (di)ethylamino each of which is optionally substituted by C$_1$–C$_4$-alkylamino, or represents phenyl or naphthyl which are optionally substituted by methoxy, or
Y together with the radical R$^1$ represents —CH$_2$— or —CH$_2$CH$_2$—,
n represents 0 or 1,
X represents hydrogen, chlorine, bromine, methyl or ethyl, and
m represents 1, 2 or 3.

Compounds of the formula (I) are very particularly preferred in which
R$^1$ represents hydrogen, fluorine, chlorine, methyl or methoxycarbonylethyl,
R$^2$ represents hydrogen or methyl,
R$^3$ represents hydrogen,
R$^4$ represents hydrogen,
A represents —CH$_2$—,
Y represents ethoxy, amino or 2-(N,N-diisopropylamino)-ethylamino,
n represents 1, and
m represents 3.

Likewise particularly preferred are compounds of the formula (I) in which
R$^1$ represents hydrogen, fluorine, chlorine, methyl or methoxycarbonylethyl,
R$^2$ represents hydrogen or methyl,
R$^3$ represents hydrogen,
R$^4$ represents hydrogen,
Y represents phenyl which is optionally substituted by methoxy, or
Y together with the radical R$^1$ represents —CH$_2$CH$_2$—,
n represents 0, and
m represents 3.

For example, using 5-(trifluoromethyl)-5-methylpyrrolidin-2-one and ethyl 2-bromoacetate as starting compounds, the process according to the invention for the preparation of the compounds (Ia) can be represented by the following formula scheme:

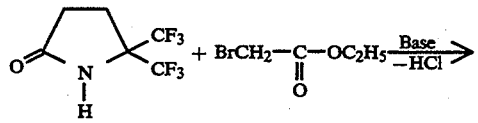

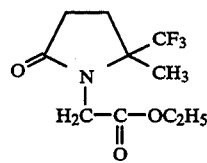

A general definition of the pyrrolidinone derivatives used as starting materials in the process according to the invention for the preparation of compounds of the formula (Ia) is given by the formula (II).

In formula (II), $R^1$, $R^2$, $R^3$, $R^4$, X and m preferably or in particular have that meaning which was already given above in connection with the description of the compounds of the formula (I).

The compounds of the formula (II) are known or can be prepared in analogous manner to the compounds already known (cf. e.g. DE-A 4 029 054).

For example, using 5-(trifluoromethyl)-5-[(2-methoxycarbonyl)eth-1-yl]-pyrrolidin-2-one as a starting compound, and reacting it in succession with aqueous sodium hydroxide solution, hydrochloric acid and acetic anhydride, the process according to the invention for the preparation of compounds of the formula (Ib) can be represented by the following synthesis scheme:

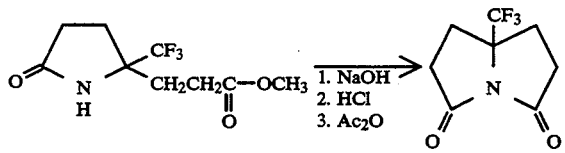

A general definition of the pyrrolidinones of the formula (IV) used as starting materials in the process according to the invention for the preparation of compounds (Ib) is given by the formula (IV). In formula (IV), the radicals $R^2$, $R^3$, $R^4$, X and m preferably or in particular have the meanings already mentioned above for compounds of the formula (I).

The compounds of the formula (IV) are new and are likewise a subject of the present invention.

Using, for example, ethyl 2-[5-(trifluoromethyl)-5-methylpyrrolidin-2-one]acetate and ammonia as starting compounds, the process according to the invention for the preparation of compounds of the formula (Ic) can be represented by the following formula scheme:

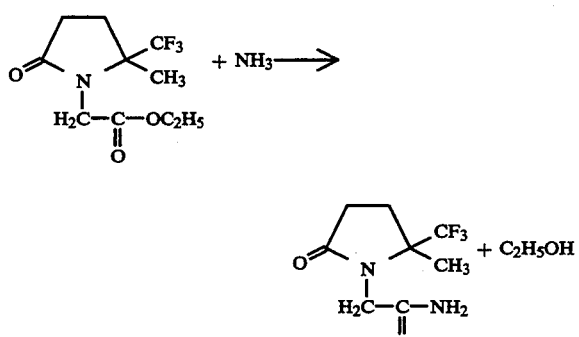

The compounds of the formula (Id) used in the preparation of compounds of the formula (Ic) are new compounds according to the invention and can be obtained by the process indicated for the compounds (Ia).

Using, for example, ethyl 2-[5-(trifluoromethyl)-5-methylpyrrolidin-2-one]acetate and N,N-diisopropylethylenediamine as starting compounds, the process according to the invention for the preparation of compounds of the formula (Ic) can be represented by the following formula scheme:

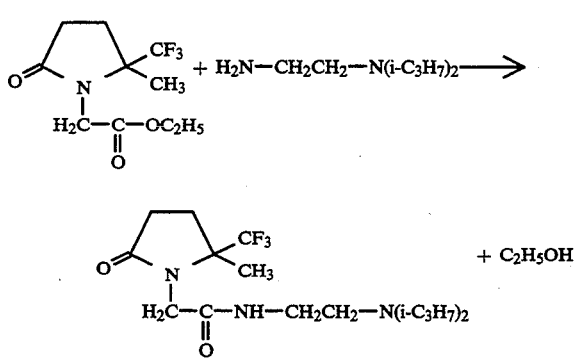

The preparation of the N-substituted α-fluoroalkyllactams of the formula (Ia) according to the invention can be carried out in the presence of a diluent. Suitable diluents are all inert organic solvents. These include, in particular, aliphatic and aromatic compounds, such as benzine, benzene, toluene, xylene, methylene chloride, chloroform, carbon tetrachloride, chlorobenzene and o-dichlorobenzene, ethers, such as diethyl ether, diisopropyl ether, dioxane and tetrahydrofuran, ketones, such as acetone, butanone, methyl isopropyl ketone and methyl isobutyl ketone, nitriles, such as acetonitrile and propionitrile, and the highly polar solvents dimethyl sulphoxide and hexamethylphosphoric triamide.

The process according to the invention for the preparation of compounds (Ia) is preferably carried out in the presence of a suitable acid-binding agent. Suitable such agents are all inorganic and organic bases which are customarily used. It is preferred to use alkali metal alcoholates, such as sodium or potassium tert-butylate, sodium or potassium tert-amylate, alkali metal carbonates such as, for example, sodium carbonate, potassium carbonate and sodium hydrogen carbonate, and also lower tertiary alkylamines, cycloalkylamines or arylalkylamines, such as, for example, triethylamine, N,N-dimethyl-benzylamine, and also pyridine, and 1,5-diazabicyclo[4.3.0]-non-5-ene and 1,4-diazabicyclo-2.2.2]-octane.

The reaction temperatures in the process according to the invention for the preparation of the compounds (Ia) can be varied over a wide range. It is in general carried out at temperatures of between −30° C. and 200° C., preferably at temperatures between 0° C. and 130° C.

When carrying out the process according to the invention for the preparation of compounds (Ia), the reaction of compounds (II) with (III) is carried out using one of the abovementioned acid-binding agents, optionally in the presence of a phase-transfer catalyst such as, for example, quaternary ammonium or phosphonium salts, in one of the abovementioned diluents. The reaction mixture is stirred at the required temperature for a number of hours.

The working-up of the reaction mixture and the isolation of the reaction products of the formula (Ia) according to the invention are carried out in a manner which is generally conventional.

The preparation of the N-substituted α-fluoroalkyl-lactams of the formula (Ib) according to the invention is carried out by reacting compounds of the formula (IV) with a base.

Suitable bases in this respect are, for example, alkali metal hydroxides such as sodium or potassium hydroxide, alkali metal carbonates such as, for example, sodium carbonate, potassium carbonate and sodium hydrogen carbonate. It is preferred to use alkali metal hydroxides such as sodium or potassium hydroxide. The base is generally employed in an amount of from 1 to 10 mol, preferably from 1 to 5 mol, per mole of the compound of the formula (IV).

The following substances are suitable for the subsequent reaction with a water-binding substance: dicyclohexylcarbodiimide, N,N'-carbonyldiimidazole, N-ethoxycarbonyl-2-ethoxy-1,2-dihydroquinoline, $BF_3$ etherate, $POCl_3$, $TiCl_4$, aliphatic and aromatic acid anhydrides such as, for example, acetic anhydride and propionic anhydride. Acetic anhydride is preferably used.

The process according to the invention for the preparation of the compounds (Ib) is in general carried out in the presence of a diluent. Suitable diluents in this respect are the diluents already mentioned above for the preparation of the compounds (Ia). It is preferred to use aliphatic and aromatic diluents, such as benzine, benzene, toluene, xylene, methylene chloride, chloroform, carbon tetrachloride, chlorobenzene and o-dichlorobenzene, ethers, such as diethyl ether, diisopropyl ether, dioxane and tetrahydrofuran, ketones, such as acetone, butanone, methyl isopropyl ketone and methyl isobutyl ketone, nitriles, such as acetonitrile and propionitrile, and the highly polar solvents dimethyl sulphoxide and hexamethylphosphoric triamide.

The reaction temperatures in the process according to the invention for the preparation of the compounds (Ib) can be varied over a wide range. In general they are from −30° to 200° C.

To carry out the process according to the invention for the preparation of the compounds (Ib), compounds having the formula (IV) in water or in mixtures of water and alcohol are admixed with a base and stirred for a number of hours at the required temperature. After removal of the solvent, the free acid is obtained by adding an inorganic acid, for example hydrochloric acid, and then drying. The ring closure is carried out by stirring with a water-binding substance at the required temperature.

The working-up and isolation of the products (Ib) according to the invention is carried out in a manner which is generally conventional.

The preparation of the compounds (Ic) according to the invention can be carried out in the presence of an inert diluent. Suitable compounds in this respect are, in principle, the diluents already mentioned above in general and as preferred in the preparation of the compounds (Ia).

The process according to the invention for the preparation of compounds (Ic) is in general carried out at temperatures of between −10° C. and 200° C. preferably between 20° C. and 150° C.

When carrying out the process according to the invention the amine of the formula (V) is in general employed in an amount of from 1 to 50 mol, preferably from 1 to 20 mol, based on 1 mol of the compound of the formula (Id).

The working-up and isolation of the products (Ic) according to the invention is carried out in a manner which is generally conventional.

The compounds of the formula (III) and the amines of the formulae (V) and (VI) are compounds which are known in general in organic chemistry.

The active substances of the formula (I) according to the invention display a strong action against pests and can be employed in practice for combating unwanted harmful organisms. The active substances are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the terms listed above may be mentioned by way of example, but not by way of limitation:

Pythium species, such as, for example, *Pythium ultimum*; Phytophthora species, such as, for example, *Phytophthora infestans*;

Pseudoperonospora species, such as, for example, *Pseudoperonospora humuli* or *Pseudoperonospora cubensis*; Plasmopara species, such as, for example, *Plasmopara viticola*;

Peronospora species, such as, for example, *Peronospora pisi* or *P. brassicae*;

Erysiphe species, such as, for example, *Erysiphe graminis*;

Sphaerotheca species, such as, for example, *Sphaerotheca fuliginea*;

Podosphaera species, such as, for example, *Podosphaera leucotricha*;

Venturia species, such as, for example, *Venturia inaequalis*;

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus*;

Puccinia species, such as, for example, *Puccinia recondita*;

Tilletia species, such as, for example, *Tilletia caries*; Ustilago species, such as, for example, *Ustilago nuda* or *Ustilago avenae*;

Pellicularia species, such as, for example, *Pellicularia sasakii*;

Pyricularia species, such as, for example, *Pyricularia oryzae*;

Fusarium species, such as, for example, *Fusarium culmorum*;

Botrytis species, such as, for example, *Botrytis cinerea*;

Septoria species, such as, for example, *Septoria nodorum*;

Leptosphaeria species, such as, for example, *Leptosphaeria nodorum*;

Cercospora species, such as, for example, *Cercospora canescens*;

Alternaria species, such as, for example, *Alternaria brassicae* and

Pseudocercosporella species, such as, for example, *Pseudocercosporella herpotrichoides*.

The good tolerance by plants of the active substances in the concentrations necessary for combating plant diseases allows treatment of plant parts above ground, of plant stock and seed, and of the soil.

In this context, the active substances according to the invention can be employed with particularly good success for combating Phytophthora in tomatoes and Venturia species in apples.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant those liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite and diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyethylene fatty alcohol ethers, for example alkylaryl polyglycol ethers, alkylsulphonates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain from 0.0000001 to 95% by weight of active compound, preferably from 0.0001 to 90%.

The active substances according to the invention can be present in the formulations as a mixture with other known active substances, such as fungicides, insecticides, acaracides and herbicides, and as mixtures with fertilizers and growth regulators.

The active compounds can be used as such or in the form of their formulations or the application forms prepared therefrom, such as ready-to-use solutions, suspensions, wettable powders, pastes, soluble powders, dusting agents and granules. Application is in the customary manner, for example by watering, spraying, scattering, dusting, foaming, brushing on etc. It is also possible to apply the active substances by the ultra-low-volume method or to inject the active substance preparation or the active substance itself into the soil. The seed of the plants can also be treated.

In the treatment of parts of plants, the active substance concentrations in the application forms can be varied over a wide range. They are in general between 1 and 0.0001% by weight, preferably between 0.5 and 0.001%.

In the treatment of seed, the necessary amounts of active substance are in general from 0.001 to 50 g per kilogram of seed, preferably from 0.01 to 10 g.

When treating the soil, active substance concentrations of from 0.00001 to 0.1% by weight, preferably from 0.0001 to 0.02% at the site of action are required.

PREPARATION EXAMPLES

EXAMPLE 1

Ethyl 2-[5-(trifluoromethyl)-5-methylpyrrolidin-2-one]-acetate

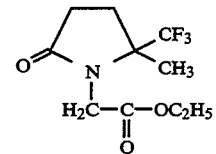

33.5 g (0.2 mol) of 5-(trifluoromethyl)-5-methylpyrrolidin-2-one are suspended in 150 ml of toluene and, after adding 30 g (0.21 mol) of powdered potassium carbonate, 2 g of tetrabutylammonium bromide and 40 g (0.24 mol) of ethyl 2-bromoacetate, are stirred for about 72 h at reflux.

The course of the reaction is monitored by GC monitoring, and if required, after about 48 h, the reaction mixture is supplemented with 5 g of potassium carbonate and optionally 8 g of ethyl 2-bromoacetate.

For working up, the reaction mixture is filtered, the salt is washed with toluene and the organic phase is concentrated in a rotary evaporator under a water pump vacuum. The crude material (52 g) is distilled under an oil pump vacuum.

17 g of a preliminary fraction with a boiling point <85°/0.02 torr were taken off containing 65% of the compound given above according to GC, and 28 g of a main fraction with a boiling point of 90°–95° C./0.02 torr, containing 95% of the desired compound according to GC, correspond to a total yield of 77%.

The compound represented above has the following NMR data:

$^1$H-NMR (in CDCl$_3$/TMS): δ=1.28 ppm; 1.49 ppm, 1.92–2.13 ppm, 2.34–2.68 ppm, 4.04 ppm and 4.19 ppm. $^{19}$F-NMR (in CDCl$_3$/CF$_3$COOH): δ=−3.3 ppm.

EXAMPLE 2

2-[5-(Trifluoromethyl)-5-methylpyrrolidin-2-one]acetamide

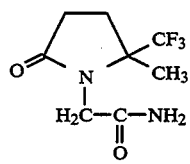

5 g (0.02 mol) of ethyl 2-[5-(trifluoromethyl)-5-methylpyrrolidin-2-one acetate of Example 1 are stirred for 18 h at room temperature in 10 ml of concentrated ammonia. The formation of amide can be followed by GC monitoring. For working up, the mixture is concentrated under a water pump vacuum, giving a highly viscous oil. The crude material (4.2 g) is distilled under an oil pump vacuum.

3.4 g of 2-[5-(trifluoromethyl)-5-methylpyrrolidin-2-one]acetamide were obtained with a boiling point of 135°–138° C./0.02 torr, corresponding to a yield of 80% of theory, having the following data:

$^1$H-NMR (in d$_6$-DMSO/TMS): δ=1.42 ppm; 1.93–2.11 ppm, 2.21–2.42 ppm, 3.78 ppm and 7.05 and 7.35 ppm. $^{19}$F-NMR (in d$_6$-DMSO/CF$_3$COOH): δ=+0.2 ppm.

EXAMPLE 3

N-[2-[Bis(1-methylethyl)amino]ethyl-2-[5-(trifluoromethyl)-5-methylpyrrolidin-2-one] acetamide

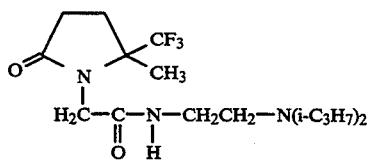

12.7 g (0.05 mol) of ethyl 2-[5-(trifluoromethyl)-5-methylpyrrolidin-2-one] acetate of Example 1 are stirred for 36 h at 130° C. with 8.6 g (0.06 mol) of N,N-diisopropylethylenediamine, during which the ethanol liberated is distilled off. Distillation is then carried out under an oil pump vacuum.

5 g of a preliminary fraction with a boiling point <110° C./0.02 torr were taken off, containing 85% of the compound depicted above according to GC, and a main fraction with a boiling point of 140°–145° C./0.02 torr which had a purity of >95% according to GC, corresponding to a total yield of 78%.

The compound obtained has the following NMR data:

$^1$H-NMR (in CDCl$_3$/TMS): δ=1.03 ppm; 1.53 ppm, 1.83–2.10 ppm, 2.32–2.54 ppm, 2.60 ppm, 3.03 ppm, 3.34 ppm, 3.97 ppm and about 6.7 ppm.

Some of the signals appear twice, due to the diastereotopy of the diisopropylamino group.

$^{19}$F-NMR (in CDCl$_3$/CF$_3$COOH): δ=−0.3 ppm.

To improve its applicability, the compound obtained is converted to the hydrochloride using aqueous hydrochloric acid.

EXAMPLE 4

Ethyl 2-[5-(trifluoromethyl)-pyrrolidin-2-one ] acetate

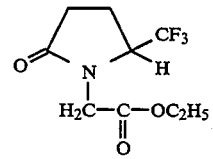

30.6 g (0.2 mol) of 5-(trifluoromethyl)-pyrrolidin-2-one are suspended in 150 ml of toluene and, after addition of 30 g (0.21 mol) of powdered potassium carbonate, 2 g of tetrabutylammonium bromide and 40 g (0.24 mol) of ethyl 2-bromoacetate, are stirred for about 36 h at reflux. The reaction is followed by GC monitoring, and if required the reaction mixture is supplemented after about 20 h with 5 g of potassium carbonate and optionally 8 g of ethyl 2-bromoacetate. For working up, the reaction mixture is filtered, the salt is washed with toluene and the organic phase is concentrated under a water pump vacuum. The crude material (46.7 g) is distilled under an oil pump vacuum.

A preliminary fraction with a boiling point <70°/0.03 torr was obtained containing 63% of the compound represented above according to GC, and a main fraction which had a purity of >96% according to GC, corresponding to a total yield of 74%.

The resulting compound has the following NMR data:

$^1$H-NMR (in CDCl$_3$/TMS): δ=1.29 ppm; 2.11–2.72 ppm, 4.19 ppm and 4.28 ppm. $^{19}$F-NMR (in CDCl$_3$/CF$_3$COOH): δ=+3.05 ppm.

EXAMPLE 5

N-[2-[Bis(1-methylethyl)amino]ethyl]-2-[5-(trifluoromethyl)-pyrrolidin-2-one] acetamide

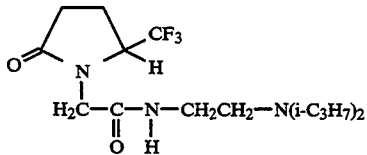

11.95 g (0.05 mol) of ethyl 2-[5-(trifluoromethyl)pyrrolidin-2-one] acetate of Example 4 are stirred 36 h at 130° C. with 8.6 g (0.06 mol) of N,N-diisopropylethylenediamine, during which the ethanol liberated is distilled off. Distillation is then carried out under an oil pump vacuum.

A preliminary fraction with a boiling point <115° C./0.02 torr was obtained, containing the compound depicted above in an amount <20% according to GC, and a main fraction with a boiling point of 132°–137° C./0.02 torr, which had a purity of >90% according to GC, corresponding to a total yield of 79.5%.

The compound obtained has the following NMR data:

$^1$H-NMR (in CDCl$_3$/TMS): δ=1.02 ppm; 2.12–2.54 ppm, 2.57 ppm, 3.02 ppm, 3.22 ppm, 4.08 ppm and 4.33 ppm. $^{19}$F-NMR (in CDCl$_3$/CF$_3$COOH): δ=+3.0 ppm.

To improve its applicability, the compound obtained is converted to the hydrochloride using aqueous hydrochloric acid.

EXAMPLE 6

2-[5-(Trifluoromethyl)pyrrolidin-2-one] acetamide

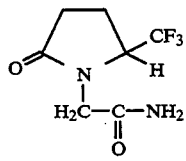

7.1 g (0.03 mol) of ethyl 2-[5-(trifluoromethyl)pyrrolidin-2-one] acetate of Example 4 are stirred for 21 h at room temperature in 10 ml of concentrated ammonia. Formation of a precipitate is rapid, and after about 4 h the reaction mixture is difficult to stir and a further 5 ml of H$_2$O are added. The solid is subsequently filtered off cold with suction, and 3.8 g of pure amide having an m.p.: 153°–155° C. are isolated.

After concentration of the mother liquor to about 30%, a further 1.3 g of the amide having an m.p.: 151°–153° C. is obtained.

Yield: 5.1 g, corresponding to 81% of theory. $^1$H-NMR (in CDCl$_3$/TMS): δ=1.97–2.10 ppm; 2.21–2.44 ppm, 3.91 ppm, 4.38 ppm and 7.1 and 7.4 ppm. $^{19}$F-NMR (in d$_6$-DMSO/CF$_3$COOH): δ=+4.2 ppm.

EXAMPLE 7

5-(Trifluoromethyl)-1-azabicyclo[3.3.0]octane-2,8-dione

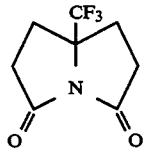

a) Hydrolysis 12 g (0.05 mol) of 5-(trifluoromethyl)-5-[(2-methoxycarbonyl)eth-1-yl]pyrrolidin-2-one and 4.5 g of a 50% strength sodium hydroxide solution are mixed in 30 ml of methanol and 15 ml of water. After the exothermic reaction has subsided, a further 10 ml of water are added, and the mixture is stirred for 16 h at reflux. After stripping off the volatile constituents there remain 17.5 g of the sodium salt.

b) Liberation of the acid

The salt is taken up in 15 ml of 20% strength hydrochloric acid and stirred for 30 min. The suspension is then taken to dryness. 19 g of acid and sodium chloride remain.

c) Ring closure 10 ml of acetic anhydride are added carefully to the solid with ice cooling. After the reaction has subsided a further 20 ml of acetic anhydride are added, and the mixture is stirred for 16 h at reflux.

The reaction mixture is filtered while hot and the filtrate is concentrated under a water pump vacuum. The crude yield is 10.5 g, and the product is recrystallized from toluene. After filtration, 9 g of product are obtained from the mother liquor, having a melting point of 151°–153° C., and for further purification are either recrystallized from isopropanol or sublimed under a high vacuum at 80°–100° C.

Yield after crystallization from isopropanol is 7.5 g, i.e. 72% of theory. M.p.: 162°–164° C.; MS: m/e =207 (M$^{30}$). $^1$H-NMR (in CDCl$_3$/TMS): δ=2.08–2.27 ppm; 2.4–3.02 ppm. $^{19}$F-NMR (in CDCl$_3$/CF$_3$COOH): δ=−1.9 ppm. $^{13}$C-NMR (in CDCl$_3$/TMS), proton-decoupled: δ=27.6 ppm; 33.9 ppm, 69.1 ppm, 127.1 ppm, 171.8 ppm. IR (in KBr, characteristic bands of the C=O groups only): ν=1800 cm$^{-1}$ (strong, broad) and 1715 cm$^{-1}$ (medium).

EXAMPLE 8

N-(4-methoxyphenylcarbonyl)-5-(trifluoromethyl)pyrrolidin-2-one

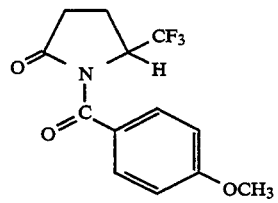

6.1 g (0.04 mol) of 5-(trifluoromethyl)pyrroldin-2-one are dissolved in 10 ml of dioxane. After the addition of 1.6 g of sodium hydroxide powder, 8.5 g (0.05 mol) of anisoyl chloride are added dropwise with stirring over a period of 10 min. The reaction is slightly exothermic and the mixture is stirred further for about 2 h.

After stirring into 50 ml of water the organic phase is separated off, if required after the addition of a little methylene chloride, and distilled under an oil pump vacuum.

8.1 g of a main fraction with a boiling point of 159–162° C./0.03 torr were obtained, corresponding to a yield of 70.4% of theory.

The product solidifies in the receiver, exhibiting a solidification point at 80°–82° C.

$^1$H-NMR (in CDCl$_3$/TMS): δ=2.21–3.03 ppm, 3.84 ppm, 5.28 ppm, 6.92 ppm and 7.71 ppm. $^{19}$F-NMR (in CDCl$_3$/CF$_3$COOH): δ=+1.7 ppm.

EXAMPLE 9

N-(4-methoxyphenylcarbonyl)-5-(trifluoromethyl)-5-methylpyrrolidin-2-one

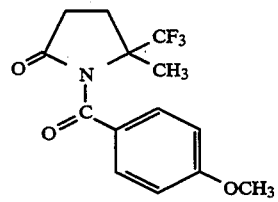

5.0 g (0.03 mol) of 5-(trifluoromethyl)-5-methylpyrrolidin-2-one in 10 ml of dioxane are stirred with 3.3 g of triethylamine and 6.8 g (0.04 mol) of anisoyl chloride for 16 h at 110°–120° C. The solid which precipitates is filtered off with suction and the salt is washed with a little dioxane. The dioxane solution is stirred into 50 ml of water and the organic phase is separated off with the addition of a little methylene chloride. After stripping off the solvent, the residue is a brownish solid which is recrystallized from ligroin.

Yield: 8.0 g, i.e. 88.6% of theory. M.p.: 94°–97° C. $^1$H-NMR (in CDCl$_3$/TMS): δ=1.82 ppm, 2.02–2.18 ppm, 2.41–2.79 ppm, 3.68 ppm, 6.89 ppm and 7.63 ppm. $^{19}$F-NMR (in CDCl$_3$/CF$_3$COOH): δ=+0.8 ppm.

EXAMPLE 10

N-(4-methoxyphenylcarbonyl)-5-(trifluoromethyl)-5-(2-methoxycarbonyleth-1-yl)pyrrolidin-2-one

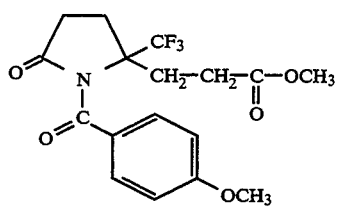

7.2 g (0.03 mol) of 5-(trifluoromethyl)-5-(2-methoxycarbonyleth-1-yl)pyrrolidin-2-one dissolved in 10 ml of dioxane are stirred with 3.3 g of triethylamine and 6.8 g (0.04 mol) of anisoyl chloride for 36 h at 110°–120° C. A whitish precipitate of NEt$_3$·HCl is slowly formed. For working up, the precipitate is filtered off with suction and the salt is washed with a little dioxane. The dioxane solution is stirred into 50 ml of water and the organic phase is separated off. A brown oil remains.

Crude yield: 8.7 g (about 60% pure according to $^1$H-NMR) Yield: 58% of theory $^1$H-NMR (in CDCl$_3$/TMS): δ=2.01–2.93 ppm, 3.64 ppm, 3.69 ppm, 6.88 ppm and 7.63 ppm. $^{19}$F-NMR (in CDCl$_3$/CF$_3$COOH): δ=+1.2 ppm.

PREPARATION OF THE STARTING COMPOUNDS

EXAMPLE 11

5-(Trifluoromethyl)-5-[(2-methoxycarbonyl)eth-1-yl]-pyrrolidin-2-one

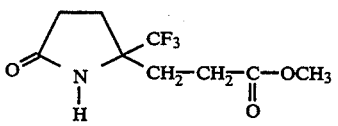

In a 0.3 l stainless steel stirred autoclave, 30.5 g (0.1 mol) of dimethyl 4-(trifluoromethyl)-4-nitropimelate in 100 ml of methanol on 5 g of 5% palladium on carbon are hydrogenated at 60–70 bar hydrogen pressure and 60° C. for about 6 h. After filtration, the methanol is stripped off at 40° C. under a water pump vacuum and the remaining mixture is subsequently stirred at 70°–80° C. under a water pump vacuum to complete the formation of the lactam. The crude yield is 23 g with a purity of about 85% (according to GC, remainder is free acid). For further purification the product is distilled under an oil pump vacuum.

19 g of a main fraction with a boiling point of 130°–137° C./0.03 torr were obtained, corresponding to a yield of 79% of theory. 3 g of residue corresponded to the free acid.

$^1$H-NMR (in CDCl$_3$/TMS): δ=1.89–2.08 ppm, 2.18–2.68 ppm, 3.69 ppm and 7.16 ppm. $^{19}$F-NMR (in CDCl$_3$/CF$_3$COOH): δ=2.0 ppm.

EXAMPLE 12

Dimethyl 4-(trifluoromethyl)-4-nitropimelate 27 g (0.465 mol) of potassium fluoride (calcined) and 86 g (1 mol) of methyl acrylate are initially charged to 50 ml of acetonitrile at 0°–5° C. and 60 g (0.465 mol) of 2,2,2-trifluoronitroethane are added dropwise with stirring over a period of 60 min. The reaction is notably exothermic (up to about 60° C.). After being cooled to room temperature the reaction mixture is further stirred for 16 h. The mixture is filtered, the salt is washed with acetonitrile, and the solvent and unreacted starting material are stripped off on a rotary evaporator.

108 g of an oil are obtained having a purity of about 92% (according to GC), which is distilled under an oil pump vacuum.

6 g of a preliminary fraction are obtained with a boiling point <120° C./0.05 torr, corresponding largely to the starting compound, and 98 g of a main fraction with a boiling point of 124°–127° C./0.05 torr, corresponding to a yield of 70% of theory.

$^1$H-NMR (in CDCl$_3$/TMS): δ=2.36–2.64 ppm, 3.71 ppm. $^{19}$F-NMR (in CDCl$_3$/CF$_3$COOH): δ=+7.5 ppm. IR (film, characteristic bands only): ν=1745 cm$^{-1}$: (strong, broad, O=C—OCH$_3$); 1570 and 1355 cm$^{-1}$ strong, NO$_2$).

USE EXAMPLES

EXAMPLE A

Phytophthora test (tomato)/protective
Solvent: 12.5 parts by weight of acetone
Emulsifier: 0.3 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are set up in an incubation cabin at 100% relative atmospheric humidity at about 20° C.

Evaluation is carried out 3 days after inoculation.

In this test, a significant superiority in activity compared with the prior art is shown by, for example, the compound according to Preparation Example 6.

TABLE A

| Phytophthora test (tomato)/protective | | |
|---|---|---|
| Active substance | Degree of untreated substance | action in % of the control at an active concentration of |
| (structure: F$_3$C-pyrrolidinone with CH$_2$NH$_2$) | 0.025 | 67 |

Example B

Venturia test (apple)/protective
Solvent: 12.5 parts by weight of acetone

Emulsifier: 0.3 part by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a significant superiority in activity compared with the prior art is shown by, for example, the compounds according to Preparation Examples 5 and 6.

TABLE B

| Active substance | Venturia test (apple)/protective | |
|---|---|---|
| | Degree of untreated substance | action in % of the control at an active concentration of |
| (structure 1) .HCl | 0.025 | 67 |
| (structure 2) | 0.025 | 89 | ally substituted $C_6$–$C_{10}$-aryl or optionally substituted $C_1$–$C_6$-alkoxycarbonyl, A represents optionally substituted $C_1$–$C_4$-alkylene, Y represents optionally substituted $C_1$–$C_6$-alkoxy, amino, optionally substituted $C_1$–$C_6$-alkylamino, optionally substituted $C_1$–$C_6$-dialkylamino or optionally substituted $C_6$–$C_{10}$-aryl, or Y together with the radical $R^1$ represents optionally substituted $C_1$–$C_4$-alkylene, n represents 0 or 1, X represents hydrogen, fluorine, chlorine, bromine or optionally substituted $C_1$–$C_4$-alkyl, and m represents 1, 2 or 3, wherein the substituents for said optionally substituted alkyl radicals, alkoxy radicals, alkylene radicals and alkoxy carbonyl radicals are fluorine, chlorine, bromine, hydroxyl, methoxy and ethoxy;

the substituents for said optionally $C_1$–$C_6$ alkylamino and substituted $C_1$–$C_6$-dialkylamino radical are $C_1$–$C_4$-alkylamino; and the substituents for said optionally substituted $C_6$–$C_{10}$-aryl are fluorine, chlorine, bromine, $C_1$–$C_4$-alkyl and $C_1$–$C_4$ alkoxy.

2. Compounds of claim 1, in which $R^1$ represents hydrogen, fluorine, chlorine, bromine, methyl, ethyl, n-propyl, i-propyl, n-butyl, s-butyl, i-butyl, t-butyl, phenyl, naphthyl, methoxycarbonylmethyl, methoxycarbonylethyl, ethoxycarbonylmethyl or ethoxycarbonylethyl, $R^2$ represents hydrogen, fluorine, chlorine, bromine, methyl, ethyl, phenyl or naphthyl, $R^3$ represents hydrogen, fluorine, chlorine, bromine, methyl or ethyl, $R^4$ represents hydrogen, fluorine, chlorine, bromine, cyano, methyl, ethyl, phenyl, methoxycarbonyl or ethoxycarbonyl, A represents —$CH_2$— or —$CH_2CH_2$—, Y represents methoxy, ethoxy, amino, or represents (di)methylamino or (di)ethylamino each of which is optionally substituted by $C_1$–$C_4$-alkylamino, or represents phenyl or naphthyl which are optionally substituted by methoxy, or

What is claimed is:

1. A α-Fluoroalkyl-lactams of the formula

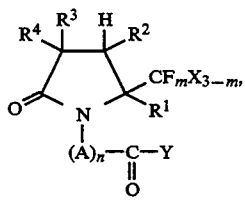

(I)

in which $R^1$ represents hydrogen, fluorine, chlorine, bromine, optionally substituted $C_1$–$C_6$-alkyl, optionally substituted $C_6$–$C_{10}$-aryl or optionally substituted $C_1$–$C_6$-alkoxycarbonyl ($C_1$–$C_4$)-alkyl, $R^2$ and $R^3$ independently of one another represent hydrogen, fluorine, chlorine, bromine, optionally substituted $C_1$–$C_6$-alkyl or optionally substituted $C_6$–$C_{10}$-aryl, $R^4$ represents hydrogen, fluorine, chlorine, bromine, cyano, optionally substituted $C_1$–$C_6$-alkyl, option- Y together with the radical $R^1$ represents —CH$_2$— or —CH$_2$CH$_2$—,
n represents 0 or 1,
X represents hydrogen, chlorine, bromine, methyl or ethyl, and
m represents 1, 2 or 3.

3. Compounds of claim 1, in which
$R^1$ represents hydrogen, fluorine, chlorine, methyl or methoxycarbonylethyl,
$R^2$ represents hydrogen or methyl,
$R^3$ represents hydrogen,
$R^4$ represents hydrogen,
A represents —CH$_2$—,
Y represents ethoxy, amino or 2-(N,N-diisopropylamino)-ethylamino,
n represents 1, and
m represents 3.

4. Compounds of claim 1, in which
$R^1$ represents hydrogen, fluorine, chlorine, methyl or methoxycarbonylethyl,
$R^2$ represents hydrogen or methyl,
$R^3$ represents hydrogen,
$R^4$ represents hydrogen,
Y represents phenyl which is optionally substituted by methoxy, or
Y together with the radical $R^1$ represents —CH$_2$CH$_2$—,
n represents 0, and
m represents 3.

5. A fungicidal composition comprising a fungicidally effective amount of a compound according to claim 1 and a diluent.

6. A method of combatting fungi which comprises applying to such fungi or to a fungus habitat a fungicidally effective amount of a compound according to claim 1.

7. The compound according to claim 1, which is of the formula

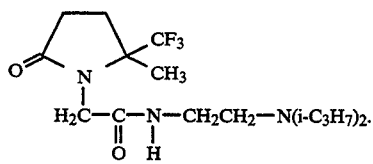

* * * * *